(12) United States Patent
Meiss

(10) Patent No.: US 8,579,833 B2
(45) Date of Patent: Nov. 12, 2013

(54) THROMBOSIS AND OSTEOPOROSIS PROPHYLAXIS

(76) Inventor: A. Ludwig Meiss, Hamburg (DE)

( * ) Notice: Subject to any disclaimer, the term of this patent is extended or adjusted under 35 U.S.C. 154(b) by 97 days.

(21) Appl. No.: 12/825,536

(22) Filed: Jun. 29, 2010

(65) Prior Publication Data

US 2010/0331740 A1    Dec. 30, 2010

(30) Foreign Application Priority Data

Jun. 30, 2009   (DE) .......................... 10 2009 031 270

(51) Int. Cl.
*A61B 5/00* (2006.01)

(52) U.S. Cl.
USPC ........................................................ 600/595

(58) Field of Classification Search
USPC .................. 600/595, 592, 587, 490, 488, 438
See application file for complete search history.

(56) References Cited

U.S. PATENT DOCUMENTS

| 5,088,503 A * | 2/1992 | Seitz ............................. 600/592 |
| 2001/0012916 A1* | 8/2001 | Deuter ......................... 600/485 |
| 2008/0254031 A1* | 10/2008 | McGowan et al. ........ 424/138.1 |
| 2008/0306410 A1* | 12/2008 | Kalpaxis et al. .............. 600/592 |
| 2011/0166480 A1* | 7/2011 | Mayer et al. .................. 600/592 |

FOREIGN PATENT DOCUMENTS

| DE | 2653556 A1 | 6/1977 |
| DE | 3306948 A1 | 8/1984 |
| DE | 29705390 U1 | 7/1998 |

* cited by examiner

*Primary Examiner* — Max Hindenburg
(74) *Attorney, Agent, or Firm* — Patent Central LLC; Stephan A. Pendorf

(57) ABSTRACT

Use of a device to reduce risk of thrombosis and osteoporosis, which uses a pressure transducer to measure the forefoot force generated by a person with their forefoot, and generates a signal so that the person can recognize whether their forefoot force has reached a minimum value.

14 Claims, 1 Drawing Sheet

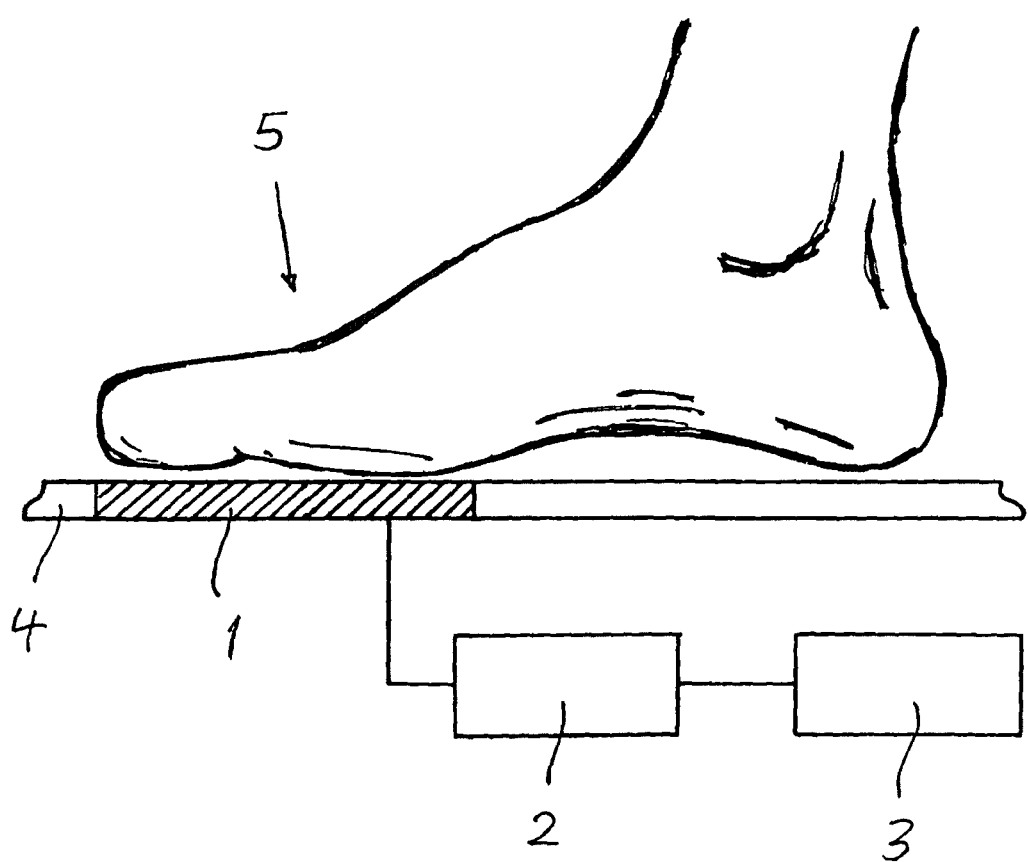

THROMBOSIS AND OSTEOPOROSIS PROPHYLAXIS

The invention relates to the use of a device for reducing the risk of thrombosis and osteoporosis.

Thrombosis is a frequently occurring condition in which a blood clot (thrombus) is formed in a vessel, usually a vein. The clot formation leads to a narrowing of the flow path and thus to a disturbance in the circulatory system. Clots may detach and become mobile. Thus, as a severe complication of a deep vein thrombosis (DVT), a massive pulmonary embolism with acute cardiac arrest could occur. In the case of an open foramen ovale (defect in the cardiac septum) a brain embolism, i.e., a stroke, is possible.

Thrombosis may result from an immobilization, such as during illness or after surgery. Increasingly, it occurs as the so-called traveler's thrombosis as, in the form of a deep vein thrombosis in the leg, and sometimes as deep vein thrombosis in the leg and the pelvis. When traveling in a car, in a plane or on a ship, a lack of exercise by the traveler, accompanied by a compression of veins, for example, the popliteal vein in the popliteal fossa (hollow of the knee) by the front edge of the seat, may lead to a reduction, in some cases a temporary halt, to of the venous return flow from the feet and lower legs. As a result of this stasis, blood clots may form in the leg and pelvic veins. For air travelers, this phenomenon is known as the "Economy Class Syndrome" because notably in narrow seats the passengers have limited freedom of movement.

In recognition of this problem, it is attempted to increase the passenger's velocity of blood flow in the leg veins, i.e. promote venous return. This can, for example, be accomplished by getting up and walking around regularly. The pressure on the feet and the activity of the leg muscles improves the blood flow (arterial as well as venous). The venous return is promoted on the one hand by the compression of the vessels in at the soles of the feet (plantar venous plexus) and on the other hand by the contractions of the lower leg muscles. The existence of a fascia system (fascial compartment system) plays of a role in the lower leg, whereby contraction of the muscles results in compression of the veins. In addition, venous one-way valves prevent blood from being carried distally, that is, away from the heart.

However, since in fully occupied airplanes, and particularly in the economy class, a frequent getting up is impractical because it disturbs the other passengers, other ways to prevent DVT are being searched for.

In DE 91 12 809 U1, therefore, a device to promote circulation in the legs is described, providing an arrangement of two pedals on a common axis, so that each pedal is pivotable about the axis against a spring force. Thereby the lower leg muscles, especially the calf muscles, are to be activated.

As has been found, however, that for an effective thrombosis prophylaxis the movement of the foot alone is not sufficient, it also requires a sufficient force be created in order to safely counter thrombosis by the "calf pump".

Powerful foot lifting exercises are not recommended, because overstressing of the muscles within the constricting fascias of the front-side lower leg (anterior and lateral compartment) might trigger the so-called "exertion- or exercise-induced compartment syndrome".

Osteoporosis presents a problem similar to thrombosis. Osteoporosis also arises due to lack of physical activity, e.g., in the elderly. If bones are not challenged by muscle tension, they wither away. They are subject to osteoporosis and can break more easily. This bone loss occurs even under conditions of weightlessness. Astronauts must therefore undergo a daily exercise program for prevention of osteoporosis, wherein the impact of the forces of on the bones becomes as effective as physical activity performed in gravity.

An example of the age-independent development of osteoporosis on earth is through physical inactivity following months to years of confinement to bed or wheelchair.

An object of the present invention is, therefore, to reduce the risk of thrombosis, particularly in passengers on land, on ships and in aircraft and also the risk of osteoporosis.

According to the invention, the solution of the problem involves the use of a device, which via a pressure sensor detects the force generated by a person with her forefoot, and provides a signal that allows the person to recognize whether her forefoot generated force has reached a minimum value.

In a preferred embodiment of the method, the forefoot force is produced by the area of the "front ball" of the feet (the heads of the metatarsal bones) and toes.

In particular, the forefoot force is generated by plantarflexion of the foot. This form of movement is associated with a contraction of the calf muscles: thus, an actuation of the "calf pump" (the body's "secondary heart"). In a powerful plantarflexion against a resistance the plantar plexus is also at least partially compressed, so that an increase of venous return through a venous inflow from the plantar plexus is facilitated.

The forefoot force is produced through the calf muscles, in particular by contraction of the gastrocnemius muscle, the soleus muscle and the toe-flexing muscles.

As it turns out, the mere movement of the foot is not sufficient for the increase in blood flow required for prevention of thrombosis. A certain amount of forefoot force must be generated, and it is of great importance to determine the amount of forefoot force. Only thereby can the venous blood return be sufficiently increased.

The forefoot force should, in particular for thrombosis prophylaxis, be dependent on the weight of the person, and each plantar flexion should be at a factor of at least 10%, preferably at least 20%, and most preferably 30-70% of the body weight.

Since the force F (expressed in Newton (N)) is proportional to mass and is dependent on acceleration, on the earth the equation would be $F=9.81$ N.

A forefoot force produced at regular intervals with half the body weight per foot would give for a person weighing 60 kg on earth at any one foot plantarflexion a forefoot force of $9.81 \times 30$, i.e., approximately 300 N.

The invention is particularly suitable for prevention of traveler's thrombosis. But it can be applied as well to thrombosis prophylaxis in bedridden or other mobility impaired people.

For prevention of osteoporosis a sufficient physical activity is also important.

The term "sufficient physical activity" is currently not well defined, but may be equated to "being sufficiently on one's legs and moving about". "Sufficient" could correspond to an average number of steps of 5000-8000 per day.

At each step there is an applied load or force of the forefoot of about 110% of the body weight, so 8,000 steps of a man weighing 60 kg result in 66 kg$\times$8,000=528,000 kg, or approximately 5.28 million N.

Generating a forefoot force can therefore also be used for prevention of osteoporosis, since the generation of a forefoot force at the same time produces the required effect on bone. Consequently, by producing forefoot forces, these step numbers can be simulated, even when sitting or lying down.

With the use of a device able to measure force in persons, there is the advantage that real physical performance, that is, force on the bone, is determined. Obviously, there is a big difference to the stress of the skeleton whether steps are made on a flat surface or whether, for example, one climbs a staircase.

According to a further embodiment of the invention is therefore envisioned that a signal is generated upon reaching a predetermined cumulative forefoot force.

In practice, one would first measure the activity output of a person and then decide whether, for prevention of osteoporosis, an increase would be advisable. One could, for example, set as a value for the total forefoot force 330,000 kg, or 3.3 million N. A 60 kg person would then have to take 5000 steps per day, with a forefoot force of 66 kg for each leg, i.e., 5000×66 kg=330,000 kg or 3.3 million N. Upon reaching 330,000 kg, or 3.3 million N, a signal would be generated. In steps with greater forefoot force, for instance when climbing stairs, a signal would be generated after a smaller number of steps, that is, sooner, in comparison to steps made with less effort on a flat surface, in which case the signal would be generated later.

For the arrangement of the pressure sensor 1, there are several possibilities. If the pressure measurement is to be done in a location-independent way, such as by aircraft passengers, it is recommended that pressure sensor 1 be provided on the foot of the passenger. This can be accomplished, for example, by mounting the pressure sensor 1 on or disposing it in a sock which is pulled over the foot or shoe of a passenger.

The pressure sensor 1 could as well be attached to an appropriate place on or in a shoe, for example, on the sole of the shoe. As shoes, there are included among others easy donning shoes like slippers or galoshes.

With such a device the person can move around freely and basically practice her thrombosis or osteoporosis prophylaxis anywhere. The forefoot 5 is simply pressed—with or without shoes—against an abutment 4, so that the pressure sensor on the forefoot can sense the resulting force. As abutment 4, it would be possible to use the floor, as well as any footrests on seats in the row ahead in vehicles, or other immovable objects.

On the other hand, it may be advantageous not to place the pressure sensor 1 on the foot of a person, but to install it directly to an abutment 4 against which the person presses her forefoot 5. Such a device can, for example, be used by several persons in succession.

In accordance with a further embodiment of the invention, the pressure sensor 1 is connected to a measuring device 2 which in turn is connected to an indicator device 3. Thus, a signal can be transmitted to the person from the indicator device 3 upon reaching a predetermined forefoot force. The person can thus optimize the foot movements necessary for prophylaxis of thrombosis and osteoporosis, as the device accurately measures the forces required, and upon reaching a predetermined value, indicates this to the person. The person is informed as to the number of active plantarflexions and the number of repetitions needed to be carried out. The person thus receives the assurance that the measures for prophylaxis of thrombosis and osteoporosis were properly and, above all, efficiently carried out.

The signal output by the indicator device can be configured optically, acoustically, or in a another way. A vibration signal has the advantage that it is less disruptive to others than, for example, an acoustic signal.

The invention will be described in detail in the following on the basis of actual test results as well as an illustrative embodiment.

Test Results

An investigation of the venous return was made by measuring the velocity of blood flow in the vein of the hollow if of the knee (popliteal vein). The maximum retrograde flow velocity (Vmax) in cm/s was measured in the right popliteal vein using Doppler sonography at rest and during distinct contraction of the calf muscles for foot plantarflexion in supine and standing positions.

The measuring instrument used was the ultrasound device LOGIQ 7 (General Electrics), 7.5 MHz transducer, 2D, color Doppler.

I. Doppler sonography in supine position on a couch.
 a. Multiple measurements at rest:
  Vmax-individual values: 13.1; 10.2; 9.9; 11.3 cm/s:
  Vmax mean: 11.1 cm/s
 b. Measurement with foot plantarflexion against a personal digital scale positioned vertically at the foot section of the couch:
  with pressure of 13 kg: Vmax 54.4 and 77 cm/s
  with pressure of 16 kg: Vmax 71.9 cm/s As the results show, foot plantarflexion against an abutment with a pressure of 13-16 kg increased the flow rate an average of about 6-fold (67.8 cm/s compared to 11.1 cm/s).

II. Measurement of the maximum retrograde flow velocity (Vmax) in cm/s in the right popliteal vein using Doppler ultrasound at rest and during contraction of the calf muscles with varying force in standing position.

To determine the foot sole pressure of the right leg, the leg was placed on a personal digital scale, and the other leg was fully loaded. In this way a weight of the right leg of 6.2 kg was measured. This value was used as the zero value in the determination of the active weight.

a. Multiple measurements at rest (i.e., simply placing the leg on the personal scale without loading it):
  Vmax-individual values: 7.7; 8.0; 8.5 cm/s:
  Vmax-mean: 8.1 cm/s
 b. Multiple measurements with foot plantarflexion against the scale with an active weight of 15 kg (i.e., after deduction of the leg weight of 6.2 kg there remained a net active weight of about 9 kg):
  Vmax-individual values: 20.9; 30.0; 30.7; 37.2; 37.2; 30.7 cm/s
  Vmax mean: 31.1 cm/s The foot plantarflexion in the standing position against an abutment with an active weight of about 9 kg led on average to an increase in flow velocity by about 3.8-fold.

c. Multiple measurements with foot plantarflexion against the scale with a total weight of 20 kg (i.e., after deduction of the leg weight of 6.2 kg there remained a net active weight of about 14 kg):
  Vmax-individual values: 39.8; 43.7; 64.0; 36.5; 18.3; 19.6; 21.2; 21.2 cm/s
  Vmax-mean: 29.4 cm/s The foot plantarflexion in the standing position against an abutment with an active weight of about 14 kg led on average to an increase in flow rate by approximately 3.6-fold.

d. Multiple measurements with foot plantarflexion against the scale with a total weight of 25 kg (i.e., after deduction of the leg weight of 6.2 kg there remained a net active weight of about 19 kg):
  Vmax-individual values: 42.4; 32.6; 41.8; 34.6; 43.7; 31.3; 34.6 cm/s
  Vmax-mean: 37.3 cm/s The foot plantarflexion in the standing position against an abutment with an active weight of about 19 kg led on average to an increase in flow velocity by about 4.6-fold.

e. Multiple measurements with foot plantarflexion against the scale with a total weight of 30 kg (i.e., after deduction of the leg weight of 6.2 kg there remained a net active weight of about 24 kg):

Vmax-individual values: 36.5; 30.0; 44.4; 31.7; 46.3; 64.0; 60.7; 40.8; 65.3 cm/s Vmax-mean: 46.6 cm/s The foot plantarflexion in the standing position against an abutment with an active weight of about 24 kg on average led to an increase in flow velocity by about 5.8-fold.

The fact that in 9 kg and 14 kg active weight almost the same increase in flow velocity was found might be due to inaccuracies in the production of the intended active weight.

EMBODIMENT

The FIGURE shows a device which can be used for prevention of thrombosis and osteoporosis. The foot of a person is here on a plate, which is an abutment 4. This foot is positioned such that the forefoot 5 touches a pressure sensor 1, so that the person can generate a forefoot force via the forefoot 5, which can be measured by the measuring device 2 via the pressure sensor 1. The measuring device 2 is connected to an indicator device 3, on which a signal can be displayed to the person, so that the person can recognize whether the generated forefoot force is sufficient.

In the example shown, the abutment 4 is rigid, so that a marked plantarflexion is possible only if the heel is raised. Thereby the knee is slightly lifted or the passenger is pushed back a bit on his seat. This allows the blood flow in the leg veins, which had perhaps been impaired by the pressure of a seat edge, to be further improved.

The abutment 4 can be designed to be pivoted, to allow plantarflexion with the support of the entire foot. In this case it is advisable to so design the pivoting abutment 4 that for example a strong and customizable restoring force directed against the forefoot force acts on the abutment 4.

The invention claimed is:

1. A method for reducing risk of thrombosis and osteoporosis, comprising:
   providing a pressure sensor (1) set to measure forefoot force produced by a person via their forefoot (5) and generate a signal that informs the person whether the forefoot force has reached a predetermined minimum value sufficient for reducing risk of thrombosis or osteoporosis, and
   having said person press against said sensor (1) with the forefoot (5) and generate the signal indicating to said person that the forefoot force has reached the predetermined minimum value sufficient for reducing risk of thrombosis or osteoporosis,
   wherein the signal is given upon reaching a predetermined cumulative forefoot force.

2. The method according to claim 1, wherein the forefoot force is produced via the ball of the foot and the toes.

3. The method according to claim 1, wherein the pressure sensor (1) is arranged relative to the person that the force generated by the plantarflexion of the foot and transmitted by the forefoot (5) is measured.

4. The method according to claim 1, wherein the forefoot force is generated by contraction of the calf muscles.

5. A method for reducing risk of thrombosis and osteoporosis, comprising:
   providing a pressure sensor (1) set to measure forefoot force produced by a person via their forefoot (5) and generate a signal that informs the person whether the forefoot force has reached a predetermined minimum value sufficient for reducing risk of thrombosis or osteoporosis, and
   having said person press against said sensor (1) with the forefoot (5) and generate the signal indicating to said person that the forefoot force has reached the predetermined minimum value sufficient for reducing risk of thrombosis or osteoporosis,
   wherein the pressure sensor (1) is arranged relative to the person so that the force generated by the plantarflexion of the foot and transmitted by the ball of the foot and the toes is measured,
   wherein said forefoot force corresponds to 30-70% of body weight of the person, and
   wherein the forefoot force is generated by contraction of the gastrocnemius muscle, the soleus muscle and the toe-flexing muscles.

6. A method for reducing risk of thrombosis and osteoporosis, comprising:
   providing a pressure sensor (1) set to measure forefoot force produced by a person via their forefoot (5) and generate a signal that informs the person whether the forefoot force has reached a predetermined minimum value sufficient for reducing risk of thrombosis or osteoporosis, and
   having said person press against said sensor (1) with the forefoot (5) and generate the signal indicating to said person that the forefoot force has reached the predetermined minimum value sufficient for reducing risk of thrombosis or osteoporosis,
   wherein the signal is produced upon reaching a given forefoot force which is programmed based on the weight of the person.

7. The method according to claim 6, wherein said forefoot force corresponds to at least 10% of body weight of the person.

8. The method according to claim 6, wherein said forefoot force corresponds to at least 20% of body weight of the person.

9. The method according to claim 6, wherein said forefoot force corresponds to 30-70% of body weight of the person.

10. The method according to claim 1, wherein the signal is optical, acoustic, or tactile.

11. The method according to claim 1, wherein the pressure sensor (1) is provided on or in a stocking or shoe.

12. The method according to claim 1, wherein the pressure sensor (1) is located on a fixture against which the forefoot force is exerted.

13. The method according to claim 10, wherein the pressure sensor (1) is connected with a measuring device (2), and the measuring device (2) is connected with an indicator device (3).

14. A method for reducing risk of thrombosis and osteoporosis, comprising:
   providing a pressure sensor (1) set to measure forefoot force produced by a person via their forefoot (5) and generate a signal that informs the person whether the forefoot force has reached a predetermined minimum value sufficient for reducing risk of thrombosis or osteoporosis, and
   having said person repeatedly press against said sensor (1) with the forefoot (5) and generate the signal indicating to said person that the forefoot force has reached the predetermined minimum value sufficient for reducing risk of thrombosis or osteoporosis,
   wherein the signal is given upon reaching a predetermined cumulative forefoot force.

* * * * *

UNITED STATES PATENT AND TRADEMARK OFFICE
CERTIFICATE OF CORRECTION

PATENT NO.       : 8,579,833 B2
APPLICATION NO.  : 12/825536
DATED            : November 12, 2013
INVENTOR(S)      : A. Ludwig Meiss It is certified that error appears in the above-identified patent and that said Letters Patent is hereby corrected as shown below:

In the Claims

Col. 6 lines 46-49 should read: -- The method according to claim 1, wherein the pressure sensor (1) is connected with a measuring device (2), and the measuring device (2) is connected with an indicator device (3).

Signed and Sealed this
Twenty-fourth Day of June, 2014

Michelle K. Lee
*Deputy Director of the United States Patent and Trademark Office*